(12) United States Patent
Dechev et al.

(10) Patent No.: US 11,672,675 B2
(45) Date of Patent: Jun. 13, 2023

(54) PROSTHETIC WRIST

(71) Applicant: Victoria Hand Project, Victoria (CA)

(72) Inventors: Nikolai Dechev, Victoria (CA); Joshua Coutts, Victoria (CA); Pranay Shrestha, Victoria (CA); Dirk Brussow, Victoria (CA); Michael Peirone, Victoria (CA); Kalonica Christie, Victoria (CA); Matt Treble, Victoria (CA); Andrea Chan, Victoria (CA); Michael Richards, Victoria (CA); Richard Knowlton, Victoria (CA)

(73) Assignee: Victoria Hand Project, Victoria (CA)

( * ) Notice: Subject to any disclaimer, the term of this patent is extended or adjusted under 35 U.S.C. 154(b) by 30 days.

(21) Appl. No.: 17/328,584

(22) Filed: May 24, 2021

(65) Prior Publication Data
US 2021/0275326 A1 Sep. 9, 2021

Related U.S. Application Data

(63) Continuation of application No. 15/194,460, filed on Jun. 27, 2016, now Pat. No. 11,013,620.
(Continued)

(51) Int. Cl.
*A61F 2/54* (2006.01)
*A61F 2/58* (2006.01)
(Continued)

(52) U.S. Cl.
CPC ............ *A61F 2/585* (2013.01); *A61F 2/5046* (2013.01); *A61F 2/54* (2013.01); *A61F 2/583* (2013.01);
(Continued)

(58) Field of Classification Search
CPC ............ A61F 2/585; A61F 2/583; A61F 2/80; A61F 2002/5096; A61F 2002/543
See application file for complete search history.

(56) References Cited

U.S. PATENT DOCUMENTS

| 42,515 A | 4/1864 | Spellerberg |
| 51,238 A | 11/1865 | Spellerberg |
| (Continued) | | |

FOREIGN PATENT DOCUMENTS

| DE | 102012012173 A1 | 12/2013 |
| EP | 0079593 B1 | 2/1986 |
| (Continued) | | |

OTHER PUBLICATIONS

U.S. Appl. No. 17/514,618, filed Oct. 29, 2021, Nikolai Dechev.
(Continued)

*Primary Examiner* — Bruce E Snow

(57) ABSTRACT

Prostheses include a terminal device, a back-lock mechanism, a wrist, a limb-socket, and a harness system. The terminal device can be a five-fingered mechanical hand that provides a releasable adaptive grasp, and has independently flexible fingers. The limb socket can be 3D printed using a molded model of a remnant limb. The harness strap can encircle an unaffected limb and is coupled to the terminal device with a cable so that a user can control the terminal device. The harness system can include a 3D printed harness ring that couples to the cable.

19 Claims, 14 Drawing Sheets

Related U.S. Application Data

(60) Provisional application No. 62/185,479, filed on Jun. 26, 2015.

(51) Int. Cl.
  *A61F 2/50* (2006.01)
  *A61F 2/80* (2006.01)
  *A61F 2/78* (2006.01)

(52) U.S. Cl.
  CPC .......... *A61F 2/80* (2013.01); *A61F 2002/505* (2013.01); *A61F 2002/5036* (2013.01); *A61F 2002/5049* (2013.01); *A61F 2002/5073* (2013.01); *A61F 2002/5093* (2013.01); *A61F 2002/5096* (2013.01); *A61F 2002/543* (2013.01); *A61F 2002/7862* (2013.01)

(56) References Cited

U.S. PATENT DOCUMENTS

| | | |
|---|---|---|
| 1,225,415 A | 5/1917 | Cronemiller |
| 1,247,077 A | 11/1917 | Caron |
| 1,273,461 A | 7/1918 | Corley |
| 1,298,502 A | 3/1919 | Henning |
| 1,324,564 A | 12/1919 | Pringle |
| 1,347,004 A | 7/1920 | Conrad |
| 1,365,646 A | 1/1921 | Charles |
| 1,366,453 A | 1/1921 | Henning |
| 1,385,817 A | 7/1921 | Grand |
| 1,402,709 A | 1/1922 | Albert |
| 1,458,923 A | 6/1923 | Mackenzie |
| 1,465,933 A | 8/1923 | Charles |
| 1,466,163 A | 8/1923 | Harris |
| 1,484,913 A | 2/1924 | Meredith |
| 1,507,680 A * | 9/1924 | Pecorella ............. A61F 2/583 623/61 |
| 1,507,681 A | 9/1924 | Alberto et al. |
| 1,507,683 A | 9/1924 | Alberto et al. |
| 1,569,286 A | 1/1926 | Edward |
| 1,630,277 A | 5/1927 | James |
| 1,644,833 A | 10/1927 | George |
| 1,742,269 A | 1/1930 | Mcelroy |
| 1,792,183 A | 2/1931 | Alberto |
| 1,989,960 A | 2/1935 | Wheeler et al. |
| 2,285,885 A | 6/1942 | Becker |
| 2,287,781 A | 6/1942 | Carnes |
| 2,301,009 A | 11/1942 | Becker |
| 2,364,313 A | 12/1944 | Pecorella |
| 2,425,154 A | 8/1947 | Hibbard |
| 2,433,301 A | 12/1947 | Simpson |
| 2,457,305 A | 12/1948 | Dale |
| 2,464,577 A | 3/1949 | Walter |
| 2,493,776 A | 1/1950 | Alberto et al. |
| 2,516,791 A | 7/1950 | Motis et al. |
| 2,532,732 A | 12/1950 | Sansbury |
| 2,535,489 A | 12/1950 | Edwards |
| 2,537,551 A | 1/1951 | Sansbury |
| 2,540,374 A | 2/1951 | Motis |
| 2,540,375 A | 2/1951 | Motis |
| 2,549,716 A | 4/1951 | Harold |
| 2,549,792 A | 4/1951 | Fletcher |
| 2,553,827 A | 5/1951 | Mason |
| 2,553,830 A | 5/1951 | Motis |
| 2,556,524 A | 6/1951 | Drennon |
| 2,561,383 A | 7/1951 | Larkins et al. |
| 2,572,914 A | 10/1951 | Chapman et al. |
| 2,582,234 A | 1/1952 | Conzelman et al. |
| 2,592,842 A | 4/1952 | Alderson |
| 2,626,398 A | 1/1953 | Grindle et al. |
| 2,652,570 A | 9/1953 | John |
| 2,654,891 A | 10/1953 | Robinson |
| 2,669,727 A | 2/1954 | Theodore |
| 2,706,296 A | 4/1955 | Fletcher et al. |
| 2,847,678 A | 8/1958 | Theodore |
| 2,853,711 A | 9/1958 | Becker |
| 2,859,450 A | 11/1958 | Becker |
| 2,867,819 A | 1/1959 | George |
| 2,885,686 A | 5/1959 | Giaimo |
| 3,026,534 A | 3/1962 | Brown |
| 3,107,358 A | 10/1963 | Prout |
| 3,159,847 A | 12/1964 | Prout |
| 3,258,784 A | 7/1966 | Brown |
| 3,382,506 A | 5/1968 | William et al. |
| 3,413,658 A | 12/1968 | Becker |
| 3,432,198 A | 3/1969 | Connor |
| 3,694,021 A | 9/1972 | Mullen |
| 4,038,706 A | 8/1977 | Ober et al. |
| 4,040,130 A | 8/1977 | Laure |
| 4,067,070 A | 1/1978 | Seamone et al. |
| 4,074,367 A | 2/1978 | Loveless |
| 4,084,267 A | 4/1978 | Zadina |
| 4,094,016 A | 6/1978 | Eroyan |
| 4,167,044 A | 9/1979 | Girard |
| 4,180,870 A | 1/1980 | Radulovic et al. |
| 4,232,405 A | 11/1980 | Janovsky |
| 4,291,421 A | 9/1981 | Massey et al. |
| 4,310,932 A | 1/1982 | Nader et al. |
| 4,364,593 A | 12/1982 | Maeda |
| 4,521,924 A | 6/1985 | Jacobsen et al. |
| 4,604,098 A | 8/1986 | Seamone et al. |
| 4,651,719 A | 3/1987 | Funk et al. |
| 4,685,924 A | 8/1987 | Massey |
| 4,685,928 A | 8/1987 | Yaeger |
| 4,685,929 A | 8/1987 | Monestier |
| 4,792,338 A | 12/1988 | Rennerfelt |
| 4,865,613 A | 9/1989 | Rizzo |
| 4,921,293 A | 5/1990 | Ruoff et al. |
| 4,946,380 A | 8/1990 | Lee |
| 4,957,281 A | 9/1990 | Christolear, Jr. |
| 4,990,162 A | 2/1991 | LeBlanc et al. |
| 5,080,682 A | 1/1992 | Schectman |
| 5,104,121 A | 4/1992 | Webb |
| 5,314,500 A | 5/1994 | Weddendorf |
| 5,800,571 A | 9/1998 | Carlson et al. |
| 5,800,572 A | 9/1998 | Loveall |
| 5,888,235 A | 3/1999 | Jacobsen et al. |
| 6,115,898 A | 9/2000 | Sawdon |
| 6,513,198 B2 | 2/2003 | Lu |
| 6,896,704 B1 | 5/2005 | Higuchi et al. |
| 6,913,627 B2 | 7/2005 | Matsuda |
| 7,087,092 B1 | 8/2006 | Landsberger |
| 7,112,221 B2 | 9/2006 | Harris |
| 7,361,197 B2 | 4/2008 | Winfrey |
| 7,655,051 B2 | 2/2010 | Stark |
| 7,867,287 B2 | 1/2011 | Puchhammer |
| 8,132,291 B2 | 3/2012 | Tsai et al. |
| 8,343,234 B2 | 1/2013 | Puchhammer |
| 8,608,398 B2 | 12/2013 | Mekid |
| 8,684,621 B2 | 4/2014 | Forthaus et al. |
| 8,795,387 B1 | 8/2014 | Razink |
| 9,320,621 B2 | 4/2016 | Iversen et al. |
| 9,572,688 B2 | 2/2017 | Puchhammer |
| 9,788,529 B2 | 10/2017 | Axelrod et al. |
| 2005/0006915 A1 | 1/2005 | Matsuda |
| 2005/0021155 A1 | 1/2005 | Brimalm |
| 2006/0129248 A1 | 6/2006 | Stark |
| 2006/0224249 A1 | 10/2006 | Winfrey |
| 2007/0173955 A1 | 7/2007 | Archer et al. |
| 2007/0213842 A1 | 9/2007 | Simmons |
| 2008/0188952 A1 | 8/2008 | Veatch et al. |
| 2008/0262634 A1 | 10/2008 | Puchhammer |
| 2008/0262636 A1 | 10/2008 | Puchhammer |
| 2008/0319553 A1 | 12/2008 | Puchhammer |
| 2010/0274365 A1 | 10/2010 | Evans et al. |
| 2012/0146352 A1 | 6/2012 | Haslinger |
| 2012/0150322 A1 | 6/2012 | Goldfarb et al. |
| 2013/0046395 A1 | 2/2013 | Mcleary |
| 2014/0171846 A1 | 6/2014 | Bonutti et al. |

FOREIGN PATENT DOCUMENTS

| | | |
|---|---|---|
| EP | 0635247 B1 | 11/1998 |
| EP | 1457294 A4 | 9/2006 |
| FR | 2665833 A1 | 2/1992 |

(56) References Cited

FOREIGN PATENT DOCUMENTS

| FR | 2822404 B1 | 9/2002 |
|---|---|---|
| GB | 157256 A | 6/1921 |
| GB | 2278281 A | 11/1994 |
| SU | 409715 A1 | 1/1974 |
| WO | 1985001437 A1 | 4/1985 |
| WO | 2000071060 A1 | 11/2000 |
| WO | 2003017880 A1 | 3/2003 |
| WO | 2007076763 A2 | 7/2007 |
| WO | 2012021823 A1 | 2/2012 |
| WO | 2013076683 A1 | 5/2013 |
| WO | 2013185231 A1 | 12/2013 |

OTHER PUBLICATIONS

Jeffrey Joiner, "Guidelines for the design of electromechanical hands and incorporation of compliant fingertips", 1994, National Library of Canada, Ottawa, Canada.).

"The Limbitless Arm," Enabling the Future website, retrieved on May 11, 2017 from http://enablingthefuture.org/upper-limb-prosthetics/the-limbitless-arm/, 7 pages.

"The Raptor Hand," Thingiverse website, retrieved May 11, 2017 from http://www.thingiverse.com/thing:476403, 1 page.

"The Rit Arm," Enabling the Future website, retrieved on May 11, 2017 from http://enablingthefuture.org/upper-limb-prosthetics/rit-arm/, 6 pages.

Bob Radocy, "TRS Product Catalog," Jan. 2015, available online at: http://www.trsprosthetics.com/wp-content/uploads/2015/10/TRS_CAT15-en.pdf.

De Laurentis et al., "Mechanical Design of a Shape Memory Alloy Actuated Prosthetic Hand," Est. Pub. Date 2002, p. 1-34, available at: http://engineering.nyu.edu/mechatronics/Control_Lab/bck/Padmini/Nano/Mavroidis/THC.pdf.

Dechev et al., "Multiple Finger, Passive Adaptive Grasp Prosthetic Hand," Journal of Mechanism and Machine Theory, 36: 1157-1173 (2001).

Ottobock, "MyolinoWrist 2000," Overview Page, Est. Pub. Date. 2013, available online at: https://shop.ottobock.us/Prosthetics/Upper-Limb-Prosthetics/Myo-Hands-and-Components/Myo-Wrist-Units-and-Rotation/MyolinoWrist-2000/p/10V51~52#product-documents-section.

Rochester Institute of Technology, "e-NABLE—volunteers offer prosthetic hands made for children by 3D printers", Jun. 23, 2014, YouTube, available at: https://youtu.be/T9nngOrdPkg (last accessed: Nov. 22, 2022).

* cited by examiner

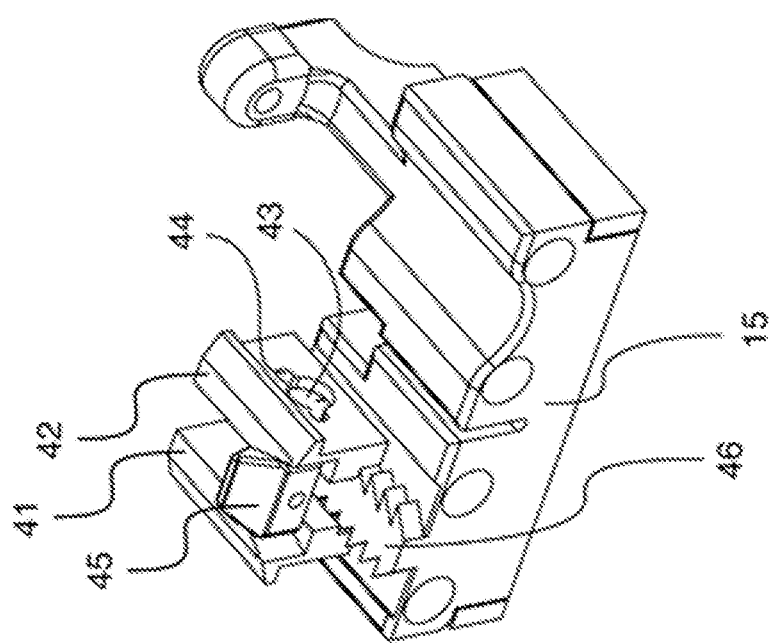
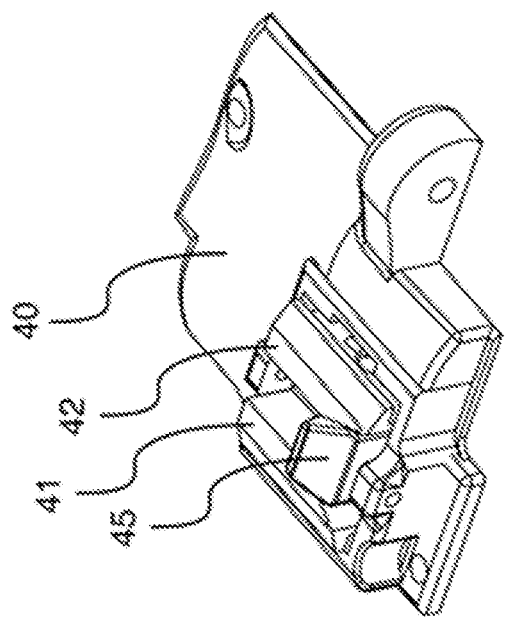
FIG. 5B
FIG. 5A

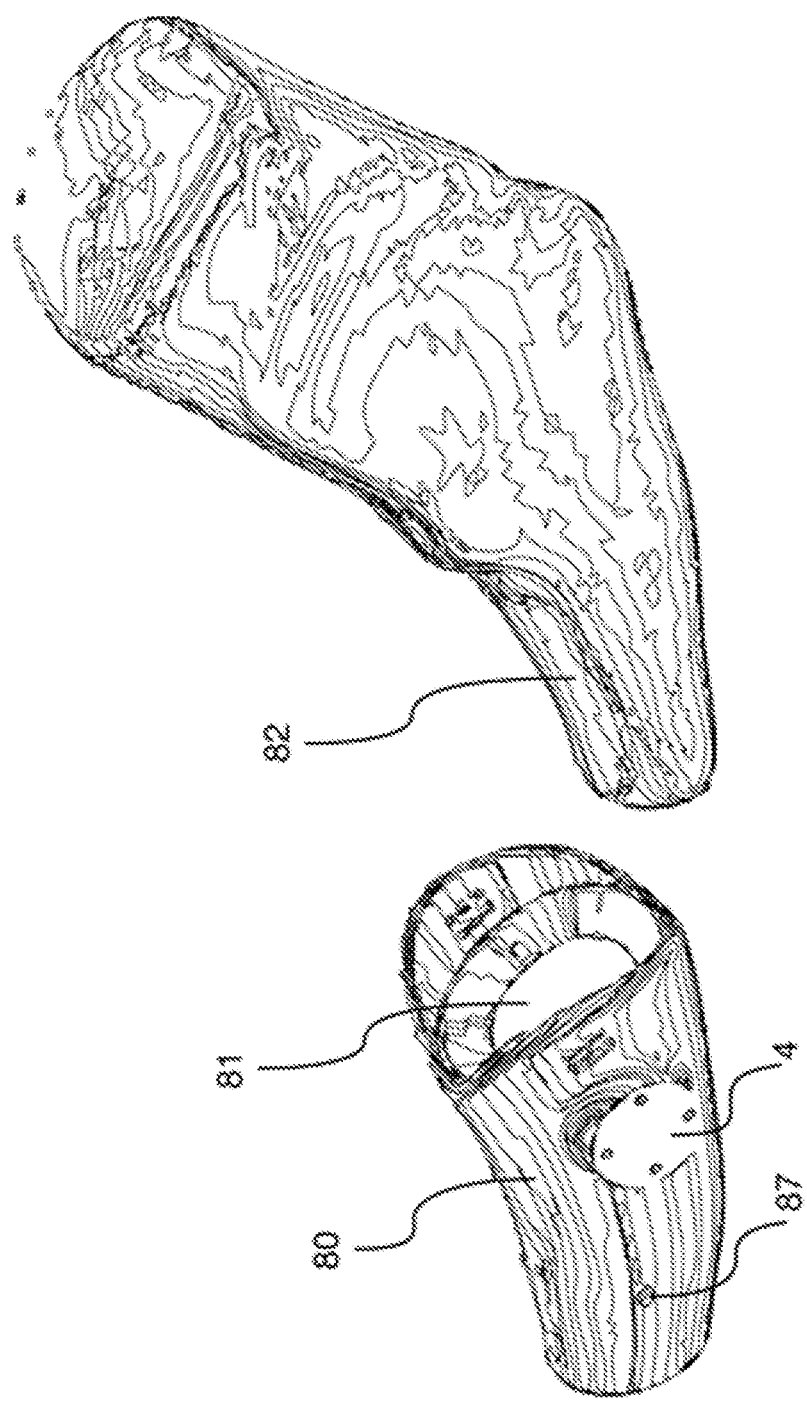

PROSTHETIC WRIST

CROSS REFERENCE TO RELATED APPLICATION

This application is a continuation of U.S. patent application Ser. No. 15/194,460, filed Jun. 27, 2016, now U.S. Pat. No. 11,013,620, claiming the benefit of priority of U.S. Provisional Patent Application No. 62/185,479, filed Jun. 26, 2015, the entireties of which are incorporated herein by reference.

FIELD

The disclosure pertains to prosthetic systems.

BACKGROUND

Prosthetic systems for the hand and wrist are devices worn on the distal end of the amputated limb. They serve to replace some of the function lost due to a hand deficiency. In some cases, persons have congenital upper-limb deficiency. There are many prosthetic hand designs, going back a few hundred years. Historically, artificial prosthetic limbs were used as a supplement for body balance, and for cosmetic purposes. Modern prosthetics allow for functional articulations and gripping of objects in addition to cosmetic appearance. Prosthetic systems today come in two categories: body-powered prosthesis and electric-powered prosthesis. A wide range of prostheses are available such as simple body-powered split-hook systems, body-powered prehensors, mechanical hands, electric-powered hands, and advanced electro-mechanical systems combining sensory feedback from the body. Prosthesis that mimic the appearance of hands are usually comprised of fingers positioned in opposition to a thumb, such that when the device is actuated, the fingers and thumb meet to form a pinch. Some prostheses are used in combination with a rotatable wrist unit to increase the mobility and mechanical function of the device.

US Publication No. 20120146352 discloses a gripping device, comprising a proximal member, a medial member, and a distal member (phalanges), which are each pivotably supported on each other. An actuator includes a motor that is coupled to a slidably supported coupling element, wherein the coupling element is arranged between the proximal member and the distal member and is connected in a force-transmitting manner both to the proximal member and to the distal member. At least one lever is arranged on the coupling element, and the lever is connected both to the proximal member and to the distal member, and kinematically couples the proximal member with the distal member. This is undesirable as the motor requires a power source and increases cost and complexity.

US Publication No. 20070213842 discloses a forearm section adapted to mount to the arm of a patient, with a hand section including a thumb and at least one finger, and a wrist section connected between the forearm section and hand section. The thumb member is rotatable. However, this is undesirable as it is powered by air springs and solenoids, increasing the cost and complexity.

US Publication No. 20130046395 discloses a hand prosthesis including a hand chassis, a thumb member mounted on the hand chassis for rotation of the thumb member in relation to the hand chassis about an axis extending generally along the length of the thumb member, and a motor disposed on the hand chassis and the thumb member. The motor is used to drive a worm and a worm gear wheel which is disposed on the other side of the hand chassis and the thumb member. The worm is in engagement with the worm gear wheel such that, upon operation of the motor, the thumb member rotates in relation to the hand chassis. This is undesirable as the motor requires a power source and increases cost and complexity.

The Toronto-Bloorview MacMillan hand experimental prosthesis has adaptive grasp. This technology lacks wrist function, customization of the socket and is not 3D printed.

There are examples of 3D printed prosthetic hands available for purchase or manufacture. The Raptor Hand is designed by e-Nable and described at http://enablingthefuture.org/upper-limb-prosthetics/the-raptor-hand/. The hand has four fingers and a thumb and is body powered through the wrists. This technology lacks an adaptive grasp, customizable socket and a wrist function. The RIT arm is designed by e-Nable and described at http://enablingthefuture.org/upper-limb-prosthetics/rit-arm/. It is body powered and has a 3-D printed socket. It can be connected to various e-Nable hands. This technology does not include a hand, and lacks customization of the socket and a wrist function.

The Limbitless Arm is designed by e-Nable http://enablingthefuture.org/upper-limb-prosthetics/the-limbitless-arm/. It has curling fingers but lacks adaptive grasp, is not body powered and lacks wrist function.

SUMMARY

The present technology is a body-powered upper limb prosthesis fabricated primarily by 3D printing. Furthermore, fabrication of the prosthesis involves "3D scanning" (image capture of 3D geometry and digitization into a scan file) of an amputee's limb geometry. Furthermore, a process is used to combine the captured 3D scan file with a generic prosthesis socket design, within a 3D computer-aided-design (CAD) environment. This process is used to produce a customized prosthesis limb-socket design that is specifically made to fit the amputee.

3D printing technology provides a way to fabricate objects represented as computer models, using plastic materials. It is also synonymous with a technology called "rapid prototyping." Typically, a 3D model/design is created on a computer using computer aided design (CAD) software, where it is visualized and stored as a computer file. When the 3D CAD model is ready, it can be printed on a 3D printer. In the past few years the price of 3D printers has dropped almost two orders of magnitude, and the quality of prints has increased substantially. As such, 3D printing technology is ideal for low-volume production of plastic parts and components, especially were some of those plastic parts require customization of each print. This is the case for prosthesis production, especially for the limb-sockets.

In some examples, prostheses systems comprise a terminal device and a wrist assembly coupled to the terminal device, the wrist assembly defining an axis of rotation, wherein the terminal device is rotatable about the axis of rotation. A limb-socket is coupled to the wrist assembly. In some examples, the terminal device is an adaptive grasp mechanism or a mechanical hand that includes at least two fingers, wherein the at least two fingers are adaptable so as to grasp an object. In some examples, the at least two fingers are passively adaptable so as to grasp an object in response to contact with the object. In other examples, the mechanical hand includes a grasp plate, and a cable is coupled to the grasp plate so that the grasp plate is urged toward the wrist assembly in response to cable tension. In alternative examples, the mechanical hand includes a force plate and extension springs coupled to the force plate and respective fingers of the mechanical hand, the force plate further coupled to a prosthesis cable so that the force plate is urged toward the wrist assembly in response to cable tension, and urged away from respective fingers by respective extension springs. In some embodiments, the at least two fingers includes a thumb, a thumb holder, and a pin that rotatably couples the thumb and the thumb holder. In additional examples, a thumb axle is coupled to the thumb holder so that the thumb holder is rotatable about an axis of the thumb holder, and a thumb piston and a thumb cylinder are coupled to the thumb holder so the thumb is adductable or abductable in response to contact with the object. In still further examples, a spring is situated within thumb cylinder and in contact with the thumb pistons so as to urge the thumb piston to extend from the thumb cylinder. In other embodiments, a pin is secured to the thumb piston, wherein the thumb cylinder defines a slot so that slidably retains the pin of the thumb piston.

In typical examples, each of the at least two fingers includes a fingertip region having at least one hole and a least one rib, and corresponding molded fingertips include molded fingertip portions that extend into the at least one hole and extend about the at least one rib. In other examples, a back lock is coupled to the grasp mechanism and includes a button release such that the back lock secures the grasp mechanism so as to retain grasp of an object by the at least two fingers, and release the grasp mechanism in response to activation of the button release. In some examples, the back lock includes a linear ratchet and at least one pawl situated to engage the linear ratchet, wherein the button release is coupled to urge the at least one pawl away from the linear ratchet in response to button activation. In still further examples, the wrist assembly includes a ball retained in a socket assembly. The ball is coupled to the terminal device or the limb socket and the socket assembly is coupled to the limb socket or the terminal device, respectively, and the ball has a central hole, wherein the cable extends through the central hole.

In some examples, the limb socket defines an interior surface corresponding to a limb portion and a tubular channel, wherein the cable extends through the tubular channel. The limb socket includes a cable rotation guide such that the cable is captured by the cable rotation guide and extends from the capture rotation guide to extend through the tubular channel. In other examples, a harness system includes a triceps brace, a cable puller bracket, a harness ring, and an axillary loop strap, wherein the triceps brace is configured to be secured to a user's upper arm and the axillary loop strap and the cable puller bracket are coupled to the harness ring, the axillary loop strap configured to encircle the user's arm. A cable is coupled to the cable puller bracket and to the axillary loop strap and is secured to the triceps brace.

Representative methods include forming a mold corresponding to a remnant limb portion and scanning the mold corresponding to the remnant limb portion to produce a surface model of the remnant limb. Based on the surface model of the remnant limb and a limb socket model, a fitted socket model is produced. At least a portion of a limb socket for the remnant limb portion is printed from the fitted socket model.

Methods include printing a harness ring that includes a ring and four buckles situated about the ring such that the four buckles are rotatable perpendicular to the ring and spinnable about the ring. The harness ring is secured to an axillary loop strap at a first selected buckle of the four buckles and a second selected buckle of the harness ring is coupled to a puller strap that is connected to a cable puller buckle.

BRIEF DESCRIPTION OF THE DRAWINGS

FIG. 5A shows a palm cover.

FIG. 5B shows a back lock mechanism within a palm cover.

FIGS. 8A-8C illustrate a representative limb socket.

DETAILED DESCRIPTION

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language. In some cases, components are referred to as "directly coupled" to indicate the absence of intermediate elements.

Figure 1:
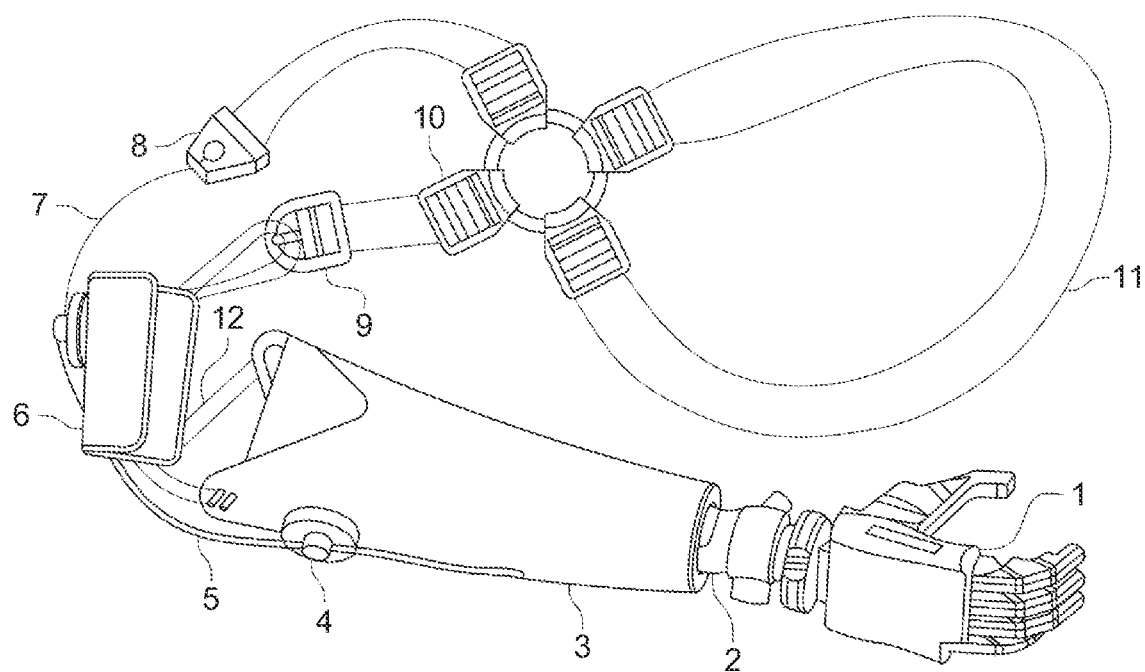
FIG. 1 shows an embodiment of the prosthesis technology.

The entire prosthesis can consist of five main systems: (a) a terminal device (five-fingered mechanical hand) 1, (b) a back-lock mechanism, (c) the wrist 2, (d) the limb-socket 3 and (e) the harness system. This disclosure pertains to systems that can combine one or more or all four of these features, along with the back-lock, into a single prosthesis system. An embodiment of the technology is shown in FIG. 1.

Terminal Device

Figure 2:
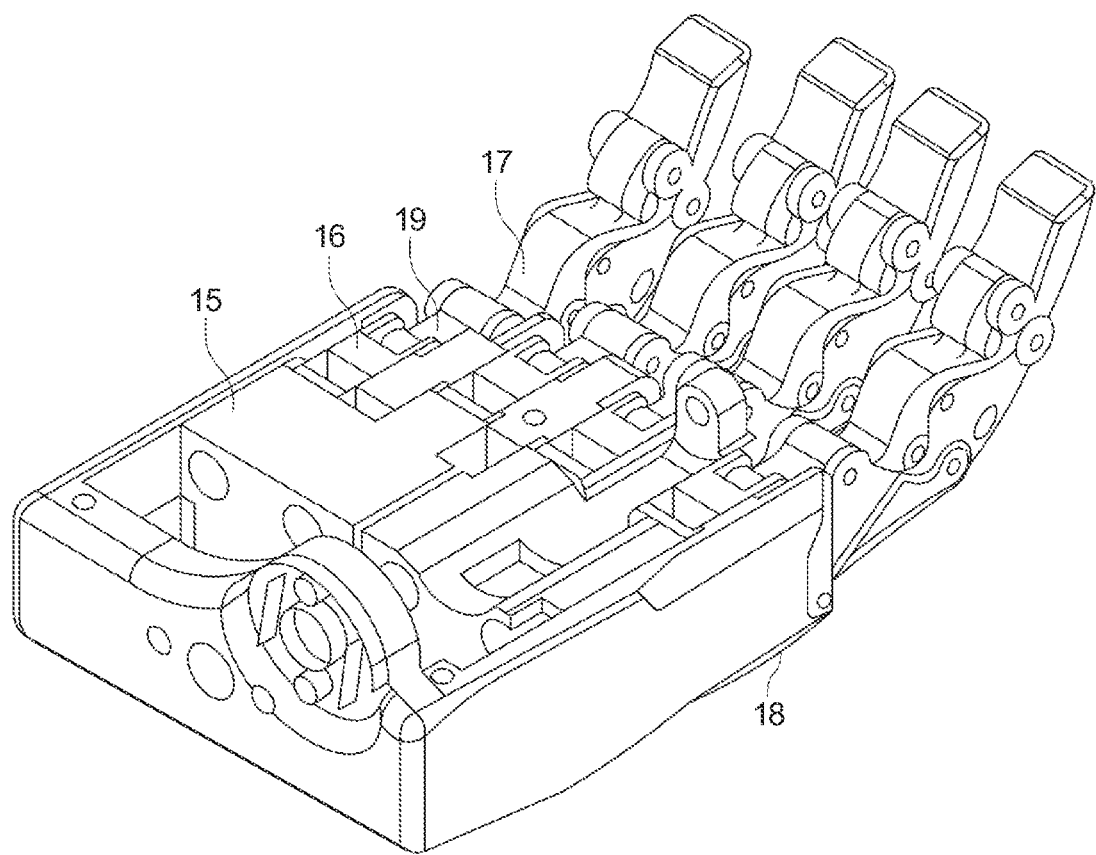
FIG. 2 shows a portion of a hand with an adaptive grasp mechanism.

The distal portion of a prosthesis used to grasp objects is called a terminal device. FIG. 2 shows a schematic of a representative embodiment of a terminal device. This embodiment includes a five-digit mechanical hand consisting of four fingers and a thumb, where all five digits flex and extend, and where the thumb is rotatable. The word flex, is terminology used to describe the closing action of a finger or limb, while the word extend is used to describe the opening action of a finger or limb. The hand has a balance between mechanical function and cosmetic appearance, hence the anthropometric geometry of the hand. The design features and properties of this embodiment of the terminal device includes a cosmetic appearance to closely resemble a natural hand, a hand design suitable for 3D printing, a hand design where any non-printed components used are standard off-the-shelf components readily available in most countries, a hand with a total weight as low as possible, and a hand sized similar to an adult female hand size.

Adaptive Grasp Technology

Figure 3:
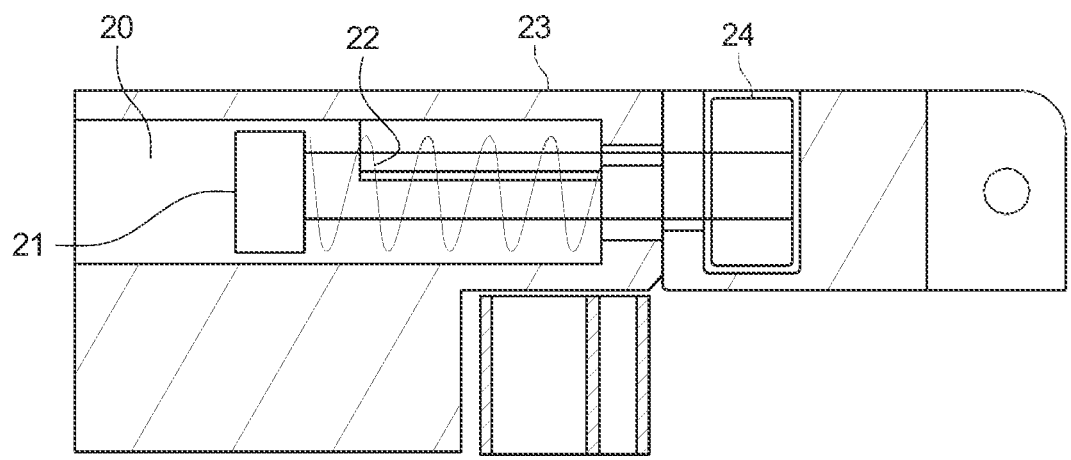
FIG. 3 shows a cross section of an adaptive grasp plate.

An embodiment of the terminal device implements three mechanical features that together give it the ability for adaptive grasp. FIG. 2 and FIG. 3 show schematics of embodiments that include adaptive grasp. First, the fingers are able to curl (change their curvature) as they flex. Second, the fingers can flex semi-independently of each other during grasping. Third, the thumb is able to adduct (rotate inwards) and abduct (rotate outwards), as well as flex and extend. The adaptive grasp feature allows the fingers and thumb to conform around the shape of various objects grasped, where the final grasp positions of the fingers and thumb will be different for each different shape or orientation of the object held. This ability of the fingers and thumb to conform around objects provides a more secure grasp on objects. This secure grasp is achieved with relatively less force applied to the object by hands with adaptive grasp, than by hands without this feature when grasping the same type of object. The adaptive grasp is mechanically passive, meaning there are no sensors or electronics used to actively coordinate finger motion. Instead, the adaptive mechanism relies on the physical contact force of the fingers with an object to adjust the positions of the fingers relative to each other.

An adaptive grasp mechanism used in this technology makes use of 3D printed parts and off-the shelf metal components to allow for a compact, complex shape, yet strong design for the mechanism. It employs a one-piece adaptive grasp plate 15 connected to the four fingers, which is 3D printed. The adaptive mechanism connects to each of the four fingers using a combination of a metal threaded bolt 21, a metal compression spring 22, a 3D printed coupler 23, and a metal lock-nut 24, to create the adaptive effect allowing for semi-independent flex of the four fingers when they grasp objects. The one-piece adaptive grasp plate has four bore holes 20. Within each hole is a metal bolt 21 that passes through a compression spring 22, where the metal bolt extends beyond the adaptive grasp plate into the coupler 23. The coupler has a lock-nut 24 rigidly embedded within, into which the metal bolt is threaded. This configuration allows for relative linear translation between the adaptive grasp plate and the coupler, whereby the compression spring creates force between the two. The coupler is in turn pinned to the finger mechanism 17 via the finger coupler 19. The prosthesis cable 7 terminates within the adaptive grasp plate, and when the amputee applies cable tension, the cable pulls toward the wrist causing the hand to flex closed.

Another way to accomplish adaptive grasp, is an alternate mechanism which allows the four fingers and thumb to flex semi-independently of each other. This can be achieved by removing the adaptive grasp plate 15, metal bolt 21, compression spring 22, coupler 23 and metal lock nut 24 from the hand shown in FIG. 2. In its place, a moving force plate is used within the palm 18, which has five extension springs attached to it. The other end of four of those extension springs is attached to each finger mechanism 17 via the finger coupler 19. The other end of the fifth extension spring is attached to the thumb 31 via a cable and pulley system. The force plate is also connected to the prosthesis cable 7, which actuates the force plate by pulling it toward the wrist causing the hand to flex and extend. Alternatively, rubber bands, elastic rubber straps, or other elastic material can be used in place of the extension springs.

Another way to accomplish adaptive grasp, is an alternate mechanism which allows the four fingers and thumb to flex semi-independently of each other. This can be achieved by removing the adaptive grasp plate 15, metal bolt 21, compression spring 22, coupler 23 and metal lock nut 24 from the hand shown in FIG. 2. In its place, a pulley and cable system can be used, along with a moving force plate. The system consists of a number of stationary idler-pulleys, a number of sliding-pulleys connected to the finger couplers 19, and a pulley cable. The pulley cable is wrapped around the pulleys in such a way that when tension is applied to the pulley cable via the force plate, each sliding-pulley can exert twice the cable tension to its finger, via the finger coupler 19. An extension spring for each finger is used to open up the fingers whenever the cable tension is relieved. With the pulley and cable system, no matter what the final grasp position of a finger is, all fingers will exert approximately the same force upon the object. The force plate is also connected to the prosthesis cable 7, which actuates the force plate by pulling it toward the wrist causing the hand to flex and extend.

Another way to accomplish adaptive grasp, is an alternate mechanism which allows the four fingers and thumb to flex semi-independently of each other. This can be achieved by removing the adaptive grasp plate 15, metal bolt 21, compression spring 22, coupler 23 and metal lock nut 24 from the hand shown in FIG. 2. In its place, a moving tilt-plate mechanism can be used. The tilt-plate has five rods attached to it by revolute joints. The other end of four of those rods is attached to each finger mechanism 17 via the finger coupler 19 using a revolute joint. The other end of the fifth rod is attached to the thumb 31 via a cable and pulley system. The moving tilt-plate is also connected to the prosthesis cable 7, which actuates the tilt-plate by pulling it toward the wrist causing the hand to flex and extend. Alternatively, a two-tiered tilt-plate system can be used, whereby the rods are attached to the second tier tilt-plates at one end, and to the finger couplers 19 at the other end.

Rotatable Thumb with Adaptive Grasp

Figure 4A:
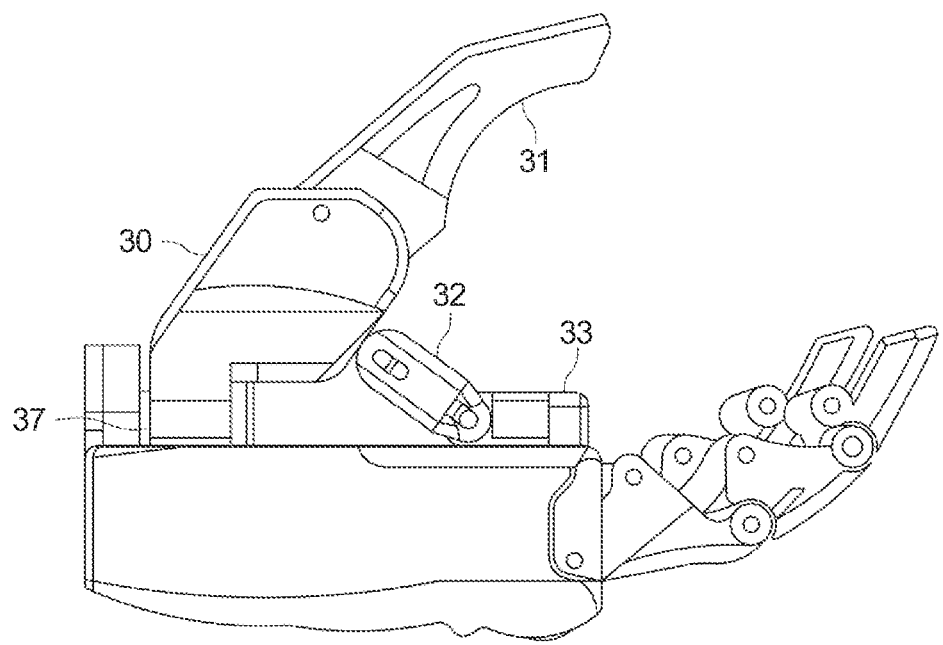
FIG. 4A shows a side view of a hand showing a thumb mechanism.
Figure 4B:
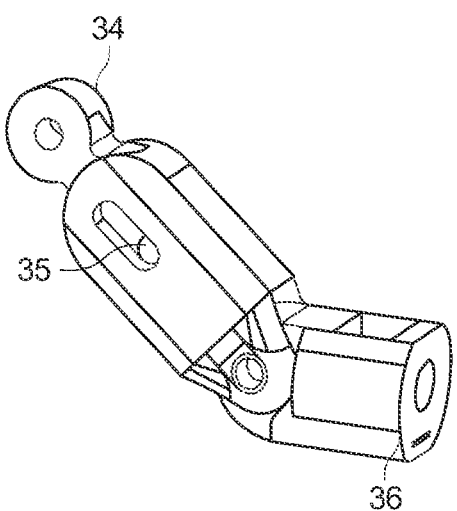
FIG. 4B shows a thumb adaptive grasp mechanism.
Figure 4C:
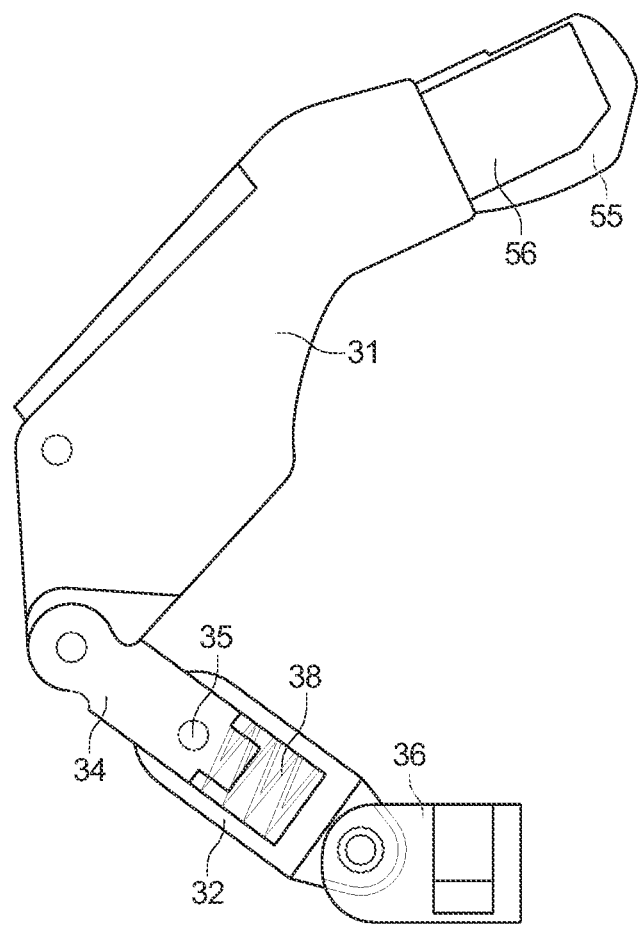
FIG. 4C shows a cross section of the thumb adaptive grasp.

FIGS. 4A-4C show an embodiment of a thumb. This embodiment combines a thumb rotation mechanism, a thumb flexion-extension mechanism, and a thumb adaptive grasp mechanism, all together into a compact and unique design. This allows the entire thumb to concurrently open and close, to adduct and abduct, and to possess the adaptive grasp function. The thumb system is configured as follows: the thumb 31 is pinned to the thumb holder 30, allowing the thumb to flex and extend about the pin. The thumb holder rotates about a thumb axle 37, allowing the thumb holder with thumb to adduct and abduct. The thumb is also connected to the thumb piston 34, which actuates the thumb to flex and extend as the thumb piston is pulled or pushed. To provide the thumb with the adaptive grasp feature, the thumb cylinder 32 and thumb piston 34 are used. The adaptive grasp cross section is illustrated in FIG. 4C, where the thumb cylinder 32 features a bore hole, in which the thumb piston 34 is inserted. This piston 34 passes through a metal compression spring 38. The thumb piston is constrained to linearly translate within the thumb cylinder, with a fixed translation distance defined by a pin-and-slot 35. The slot is on the thumb cylinder and the pin is embedded into the thumb piston. This configuration allows for relative linear translation between the thumb piston and the thumb cylinder, whereby the compression spring 38 creates a force between the two. The thumb cylinder is connected to the thumb rotational pivot 36, via a metal bolt. The thumb rotational pivot 36, the metal bolt, and the thumb axel 37 are all co-axial (share a common axis). This allows the entire combination of the thumb holder, thumb, thumb piston, and thumb cylinder to adduct or abduct about this common axis. The metal bolt connects the thumb rotational pivot 36 to the adaptive grasp plate 15, allowing the adaptive grasp plate to pull or push the thumb rotational pivot. This pull or push is transferred into the thumb cylinder and onto the thumb piston, allowing for the aforementioned flexion and extension of the thumb.

Fingertips and Thumbtips

FIGS. 4A-4C show an embodiment of a thumbtip. Compliant castable urethane-based rubber fingertips and thumbtips can be incorporated into the technology. The thumb 31 can have a tip 55 cast in urethane-based rubber or another suitable material to provide compliant grip when grasping objects. Each finger 17 can also have tips. A two-part urethane rubber compound was used for this process. The urethane is mixed at a one-to-one ratio by volume, in a batch size dependent on the number of tips to be cast. The urethane has a rubber durometer hardness of 30, but any reasonable hardness could be used depending on the application. A color pigment system is used to achieve the desired color of the urethane. This is done by gradually mixing one or more color dye pigments into the two-part urethane mix while stirring thoroughly. To cast the shape, molds are used. The molds are created by 3D printing them. The molds are two-piece and have a negative image of the shape to be cast, that is specifically designed for the finger tips or thumb tip. A mold release agent is sprayed into the fingertip molds and thumb tip mold. After the urethane is prepared, it is poured into the molds. Four fingers and one thumb tip are placed in the urethane filled fingertip and thumb-tip molds, respectively. Pin holes within the molds are lined up to pin holes in the finger and thumb. Using 2 mm pins, the fingers and thumb are held in the correct position within their molds. The filled molds are left to cure. Upon curing of the urethane, the fingers and thumb tip are removed from the molds, by splitting the molds along the parting line, and any excess urethane is trimmed away. To prevent the urethane tips from detaching from the fingers and thumb tip, two geometrical features are designed into the tips of the fingers and thumb. Each finger and thumb tip are equipped with ribs 57, and holes 58 on the exposed cast surface 56 (the portion to be covered with urethane). These ribs and holes allow the liquid urethane to flow in and form around the tip when it is being cast. When it is cured, these features keep the urethane tip attached to the finger or thumb tip. This geometry provides an increased surface area for the urethane to adhere onto, and further aids in restraining the fingertip.

Another way to accomplish complaint fingertips and thumbtips, is to use an alternate fabrication process. This can be achieved by directly 3D printing the fingertips and thumbtips, using a flexible/soft or rubber-like 3D print material. There are many different formulations of flexible/soft 3D print materials. Once the tips are printed, they can simply be put onto the fingertips and thumbtip.

Back-Lock Mechanism

Figure 5C:
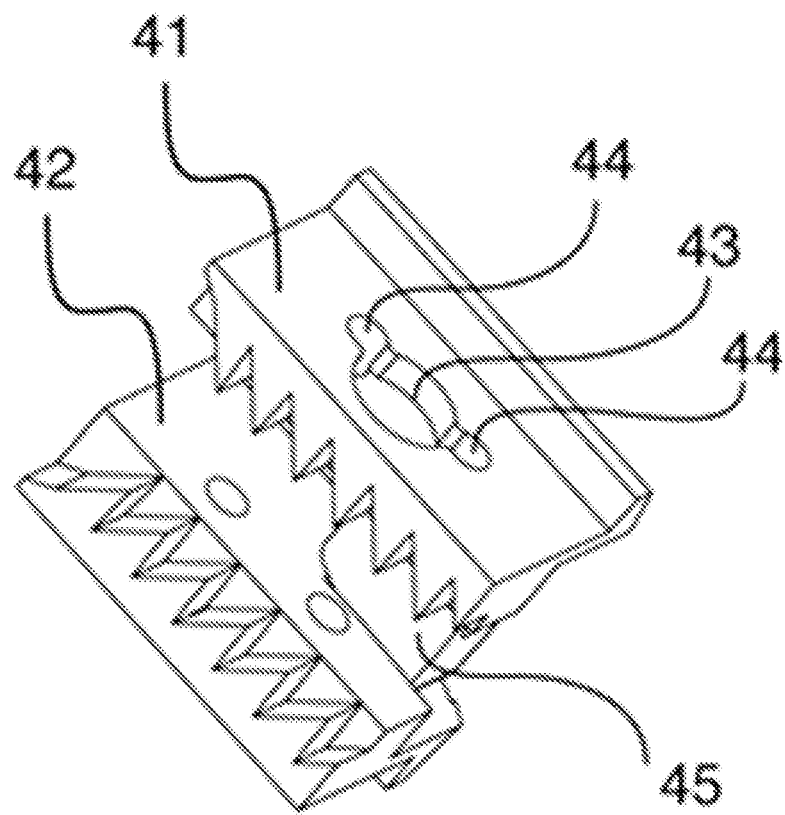
FIG. 5C shows a back lock mechanism within a palm cover.
Figure 6A:
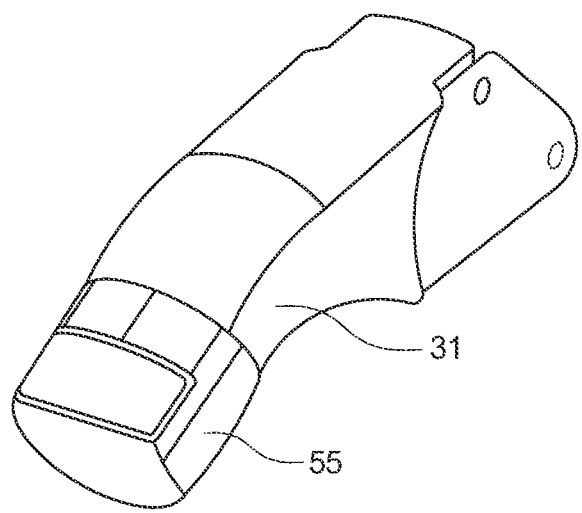
FIG. 6A shows a thumb with urethane-based rubber thumb tip.
Figure 6B:
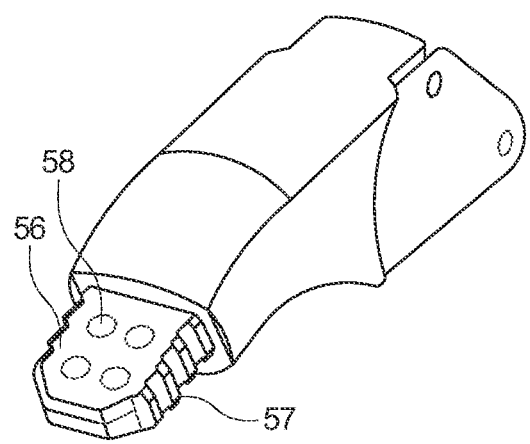
FIG. 6B shows a thumb with an exposed cast surface.
Figures 7A, 7B:
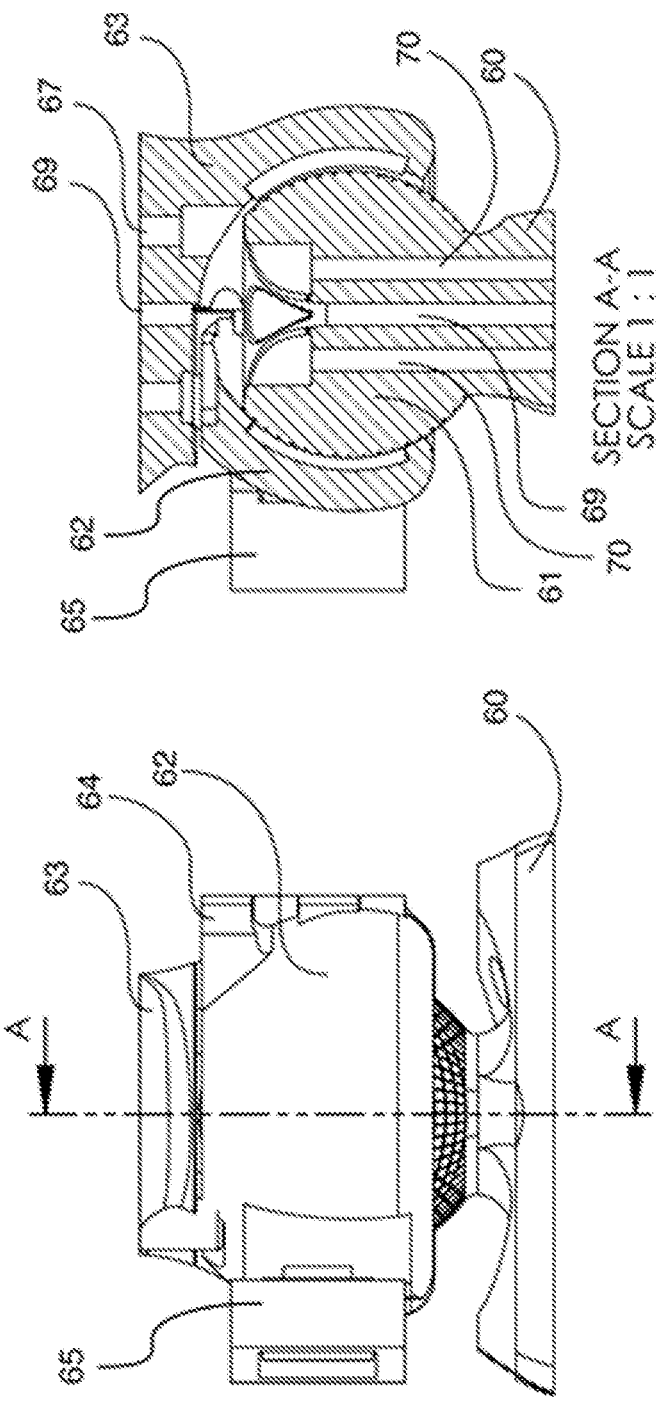
FIG. 7A shows a side view of a wrist mechanism assembly.
FIG. 7B shows an angled view of a wrist mechanism assembly.
Figure 7D:
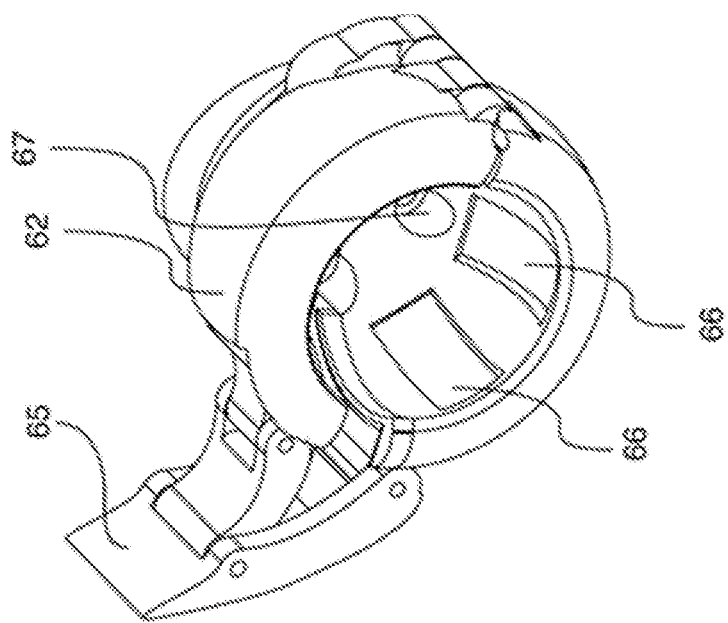
FIG. 7D shows an angled view of a socket assembly of a wrist mechanism assembly.
Figure 7C:
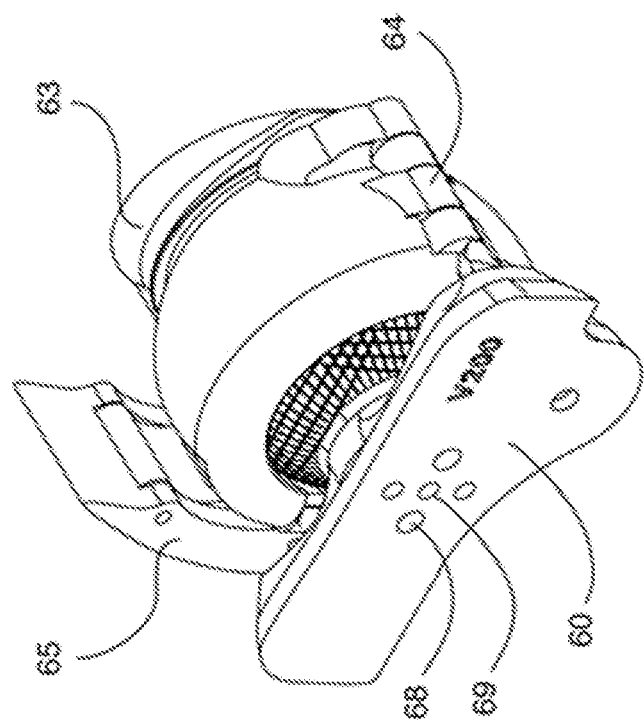
FIG. 7C shows a cross section of a wrist mechanism assembly.

FIGS. 5A-5C show an embodiment of a back-lock mechanism. The back-lock mechanism is used to switch the hand between a free grasp state, and a locked grasp state. While in a free grasp state, the fingers and thumb will only exert pinch force on a grasped object when the amputee applies tension on the prosthesis cable 7. While in a locked grasp state, the fingers and thumb will lock down onto an object, and will maintain pinch force onto it, even if the tension on the prosthesis cable 7 is released. This locked state allows the amputee to freely move their arm with no tension in the main prosthesis cable, yet the object they grasp will stay firmly within the hand.

The back-lock mechanism is housed in the palm cover 40. In one embodiment, a pawl and linear ratchet mechanism is used. This is achieved with a linear ratchet 46 connected to the adaptive grasp plate 15, along with spring-loaded pawls 41, 42 housed within the palm cover 40. There are two spring loaded pawls, a left-pawl 41, and a right-pawl 42. As the linear ratchet 46 translates past the pawls, several lock positions are achieved that prevent the reverse travel, thereby locking the grasp onto an object. A release mechanism consisting of a button 45 exists, such that the two pawls can be forced to slip out of engagement with the ratchet, thereby releasing the system and allowing the hand to open. To operate the linear ratchet back-lock, if the amputee wishes to lock the hand onto an object, they would first push the button 45 back toward the wrist, called the lock-state, to engage the left-pawl 41 and the right-pawl 42, with the linear ratchet 46. The amputee would reach toward the object with their arm and thereby apply tension to the prosthesis cable 7, which pulls the adaptive grasp plate 15 toward the wrist, to close the hand. Hence the linear ratchet 46 would also move toward the wrist, causing it to translate past the two pawls 41, 42. As the adaptive grasp plate is pulled toward the wrist, two pawls click past the teeth in the ratchet. Both pawls 41, 42 are spring-loaded in the lateral direction, via a compression spring that sits within a spring mount 43. Both the left-pawl and right-pawl slide laterally along steel rods that pass through the holes 44 in both pawls. The hand prosthesis will remain locked in place by the pawls engaged with the linear ratchet, and the amputee is free to relax the tension of the main cable, yet the object is held in place. When the amputee wishes to release the object from the grasp, they must push the button 45 toward the fingers, called the non-lock state. The button 45 is wedge shaped and will force the left-pawl and right-pawl to move laterally away from the linear ratchet, and thereby disengage them from the linear ratchet. In the non-lock state, if there is no tension in the main cable when the user relaxes, the adaptive grasp plate will return to its initial position (via its extension springs), and the hand opens up and releases the object. The button 45 will remain in either the non-lock state indefinitely, or the lock-state indefinitely, until such time as the amputee changes the states by pushing the button in either direction.

An alternative version will have the linear ratchet connected to the prosthesis cable 7, and the pawl connected to the limb-socket 3.

Another way to accomplish the back-lock mechanism, is to use a follower pin that rides within a spring-loaded slider plate that allows the hand to toggle between the locked state and free state. One end of the follower pin could be embedded into the adaptive grasp plate 15, and the other end of the pin could protrude into a follower slot within a slider plate. The follower slot would slide around a four-section-shape consisting of a guide, a lock groove, a return position, and a return path. To operate such a toggle style back-lock, if the amputee wishes to lock the hand onto an object, they reach toward the object with their arm and thereby apply tension to the prosthesis cable 7, which pulls the adaptive grasp plate 15 toward the wrist, to close the hand. Hence the follower pin would also move toward the wrist, causing it to translate within the follower slot in the slider plate. As the adaptive grasp plate is pulled toward the wrist, the pin presses against the guide, causing the slider plate to move laterally. The slider is spring-loaded in the lateral direction, via a compression spring that sits within a spring mount. When sufficient cable tension is applied, the follower pin reaches the locking position, and slips into a lock groove in the slot with a click sound. The hand would now be locked, and the amputee is free to relax the tension of the main cable, yet the object is held in place. When the amputee wishes to release the object from the grasp, they must again apply tension to the main cable. Sufficient release tension must be applied to bring the follower pin to the return-position in the slot, which is approximately 2-3 mm past the lock groove. Once the return-position is achieved, the follower pin drops into the return path of the slot, and when the user relaxes the cable tension the hand opens up and releases the object.

FIGS. 5A-5C shows an embodiment of the linear ratchet back-lock mechanism. The details of the back-lock are as follows: that the linear ratchet is attached to the adaptive grasp plate within the hand. The linear ratchet 46 moves between the left-pawl 41 and right-pawl 42. The left-pawl and right-pawl have holes 44 that allow them to slide laterally along two guide rails, and the left-pawl and right-pawl are spring loaded. The key features of the back-lock mechanism are: One compression spring to exert force on the left-pawl and another compression spring exerts force on the right-pawl, via the spring mounts 43 and create force. Two guide rails that carry the left-pawl and right-pawl and smooth out the motion of the left-pawl and right-pawl as they press against the linear ratchet. A button 45 that can de-activate or active the back-lock mechanism is part of the mechanism.

Wrist Mechanism

In one embodiment, the prosthetic wrist system is a ball-and-socket joint. A representative embodiment is shown in FIGS. 7A-7D with a two-piece wrist-socket (with upper wrist socket 62 and lower wrist socket 63) and a ball on a ball-base 60. The upper wrist socket 62 and lower wrist socket 63 are attached together on one side by a hinge 64. On the other side they are clamped together using a four-bar rocker mechanism, where one of the links is the latch 65. This clamping can be carried out by pressing the latch 65 toward the wrist, or can be unclamped (loosened) by pulling the latch 65 away from the wrist. The two-piece wrist-socket is implemented to facilitate easy flexion/extension of the hand, as well as rotation of the hand, or a simultaneous combination of both. It also facilitates easier removal of the entire hand, which could be replaced with some other type of 3D printed terminal device, that is equipped with the ball 61 portion. The clamp system (consisting of the latch 65 mechanism) can be used to change the separation between the two wrist-sockets, effectively increasing or decreasing the applied friction within the wrist (i.e. adjust the friction force between the ball and the wrist-socket by changing the normal force between them). This can also be achieved if a cam system was used as part of the latch for adjusting the separation between the wrist-sockets, or if the two wrist-sockets were screwed together from both sides (with one or both using screws and nuts). Rubber lining 66 is added in the spherical cavity of the wrist-sockets to increase overall friction force of the locking mechanism. The wrist-socket is attached (usually fastened with screws and nuts, but other connectors can be used) to the limb socket 3 via holes 67 in the lower wrist socket, and attached to the palm 18 via holes 68 in the ball-base 60.

The ball 61 of the wrist has an outer convex (spherical) surface that interfaces with the wrist-socket. A grid pattern of thin grooves on the ball is used to increase the frictional coefficient of the surface by increasing its surface roughness. The wrist can then be re-positioned by first pulling the latch 65 away from the wrist, and then the able hand of the amputee, or another force is used to re-position then hand. Next, the latch 65 is pushed back toward the wrist to lock the socket into place while the hand is in any desired orientation. The ball-base 60 is designed to hold the ball 61 and connect the wrist to the prosthetic hand or other terminal device. The ball-base 60 has a central hole 69 to allow for a cable 7 to run through it, so that the cable 7 can be attached to the adaptive grasp plate 15 within the hand. In addition, the ball-base is reinforced using two, three, or four 2 mm stainless pins that run axially through the ball 70 to add strength to the wrist.

One embodiment of the wrist is designed to have the following features: a wrist suitable for 3D printing, where any non-printed components are standard off-the-shelf components readily available in most countries, a wrist that is entirely mechanical, a wrist that maximizes the degrees of freedom in three axes of rotation (namely pronation-supination, flexion-extension, and radial-ulnar deviation), a wrist that is compact and lightweight, and a wrist with adjustable locking force (or adjustable friction).

In addition to the features mentioned above, the wrist is also designed to be intuitive and easy to use. More specifically, it enables one-handed operation of the wrist whereby the amputee uses their remaining able-hand to articulate the wrist to the desired orientation. It enables an easy unlocking latch mechanism, and allows for easy positioning of the wrist to any desired position. The latch can be opened in one single grasp using an able hand, thus releasing the friction lock. The wrist can then be positioned to the desired orientation by moving the palm to the desired orientation. Next the latch is closed thus securing the wrist in the altered orientation. Hence, the wrist can be unlocked and re-positioned by a single grip-and-move action of the able hand, ensuring intuitive and easy use by the user.

Limb Socket

Figure 8B:
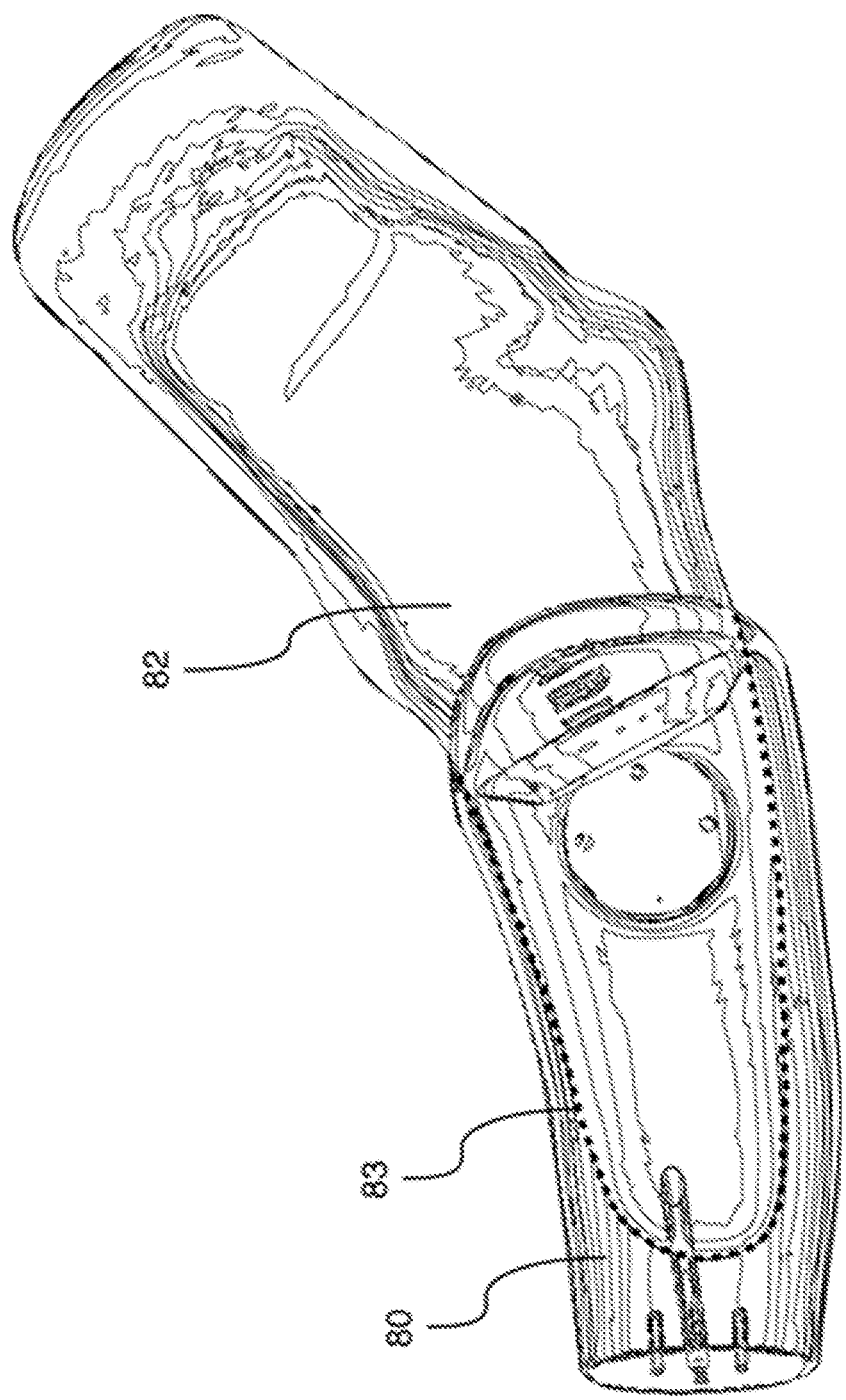

The 3D printed limb-socket 3 can be created by computer aided design (CAD), whereby a generic 3D model 80 and a 3D scan of the amputee's limb (3D surface model of the remnant limb) 82 are manipulated and combined together within the CAD software. The generic 3D model 80 is a solid 81 model created with equation driven parameters, and can be customized depending on the limb geometry of the amputee. Input parameters include wrist circumference, forearm circumference, wrist-to-elbow length, and a width adjuster parameter. The cable 7 that passes along the limb-socket travels through the cable housing 5 which in turn passes through a tubular channel 87 within the limb-socket 3. The cable rotation guide 4 is built directly into the side of the limb-socket. This allows the cable housing to pivot freely, depending on the position of the amputee's arm. The cable housing passes along the outside of the limb-socket and then enters the limb-socket through a tubular channel 87 that is created in the limb-socket. The cable housing ends at the center of the wrist. The limb-socket has built in tie points for the straps 12 which connect the limb-socket 3 to the triceps brace 6. The straps can be adjusted depending on the individual anatomy of the patient. The end of the limb-socket may alternatively include a standard ½-20 bolt hole which can be used for attaching terminal devices of other styles. The interior shape/form 85 of the limb-socket is customized to each different amputee using 3D laser scanning to capture a 3D surface model of the remnant limb 82. The 3D surface model of the remnant limb 82 is combined with the generic 3D model of the socket 80 using CAD as shown in FIG. 8B, whereby a 3D boundary 83 is created at the 3D intersection of the generic 3D model of the socket 80 and 3D surface model of the remnant limb 82. A Boolean 3D subtract function is used, such that a hollow volume 86 with a surface 85 matching that shape of the 3D surface model of the remnant limb 82, is created within the generic 3D model of the socket. The resulting combined model is 3D printed to create the limb-socket 3, which is then fit onto the patient.

Figure 8C:
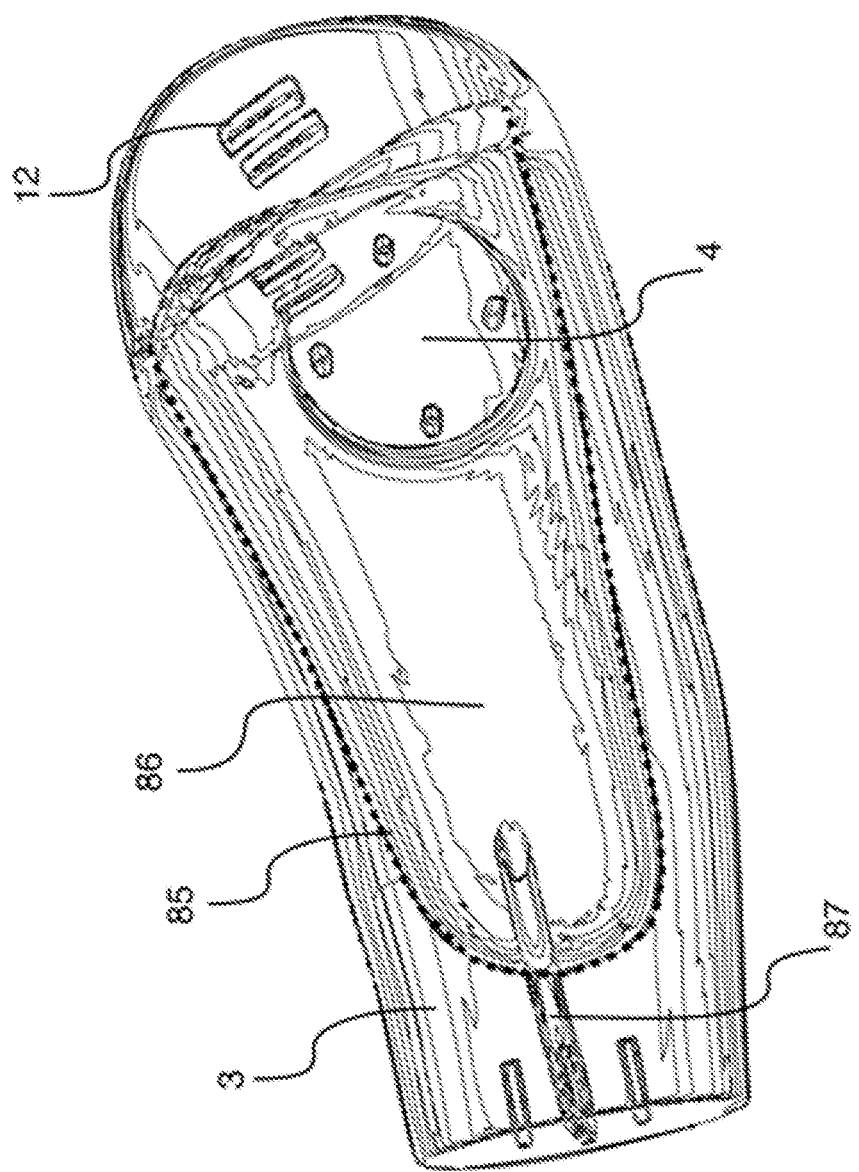

FIGS. 8A-8C shows an embodiment of the 3D printed limb-socket 3, as well as the process used to generate it using CAD with a generic 3D model of the socket 80 as well as a 3D surface model of the remnant limb 82.

The Harness System

One embodiment of the harness system uses all 3D printed components, nylon ribbons, and a unique 3D printed ring-and-buckle design. The system works by having the amputee place their remnant limb into the socket, and then cupping the triceps brace 6 onto their triceps. Their opposite arm passes through the axillary loop strap 11, which is positioned over their shoulder. The cable housing 5 serves to protect the cable 7. The triceps brace 6 is connected to the socket 3 with the socket straps 12 ribbon. The triceps brace is also connected to the triceps buckle 9 by a strap. The triceps brace 6 also serves to anchor the position of cable housing, which passes through the cable rotation guides. The cable puller buckle 8 is connected to the end of cable 7, which enables tension force to be transferred from the harness assembly through the cable 7 to the hand 1. The cable puller buckle 8 is attached to the harness ring 10 by a strap. The harness ring connects to the cable puller buckle 8, and to the triceps buckle 9, by separate straps, and to the axillary loop strap 11. The axillary loop strap 11 encircles the user's unaffected arm and serves to both anchor the entire device and to transmit force to the device. The harness ring 10 can be entirely 3D Printed in a continuous print, where the four buckles on the harness ring are printed in place, without fasteners. The four buckles can spin around the ring, or rotate perpendicular to the ring, but can never be removed since they are each printed as a solid piece around the ring.

Heat Treatment

Heat treatment of the 3D printed parts can be used to improve fit of the prosthetic and improve the strength of the components Annealing (heat based) of the 3D printed parts in an oven was found to greatly improve strength. Since the 3D printed parts are produced layer by layer on the printer, the adhesion from layer to layer may have variations for several reasons. After a part is printed, if it is placed into an oven and annealed (at an appropriate temperature), the layers will have an opportunity to better adhere to one-another.

Using a heat gun to apply hot air to the inside of the limb-socket can allow adjustments to better fit the remnant limb of amputees. If there are any pressure points during the fitting, the limb-socket can be removed from the amputee, and heat applied (hot air at approximately 200 degrees C.) to appropriate area of the limb-socket that is causing pressure on the limb. The socket will be heated until it is malleable, and the prosthetist will manually hand form the appropriate area of limb-socket. The limb-socket is then checked for fit, and the process of heating and forming is repeated until desired fit is achieved.

The Process to Fabricate the Limb Socket

The following is the process to 3D Scan and fabricate the 3D prosthesis limb-socket.

Figure 9:
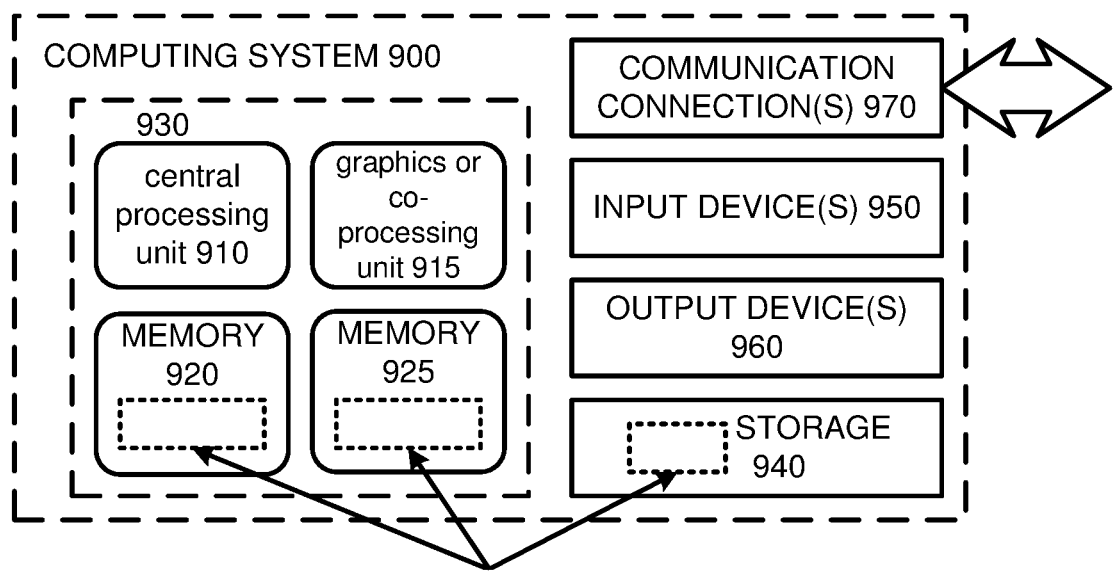
FIG. 9 illustrates a general computing system that can implement procedures for prosthesis fabrication.

- Prosthetist places a fabric sock onto the amputee's remnant limb
- Prosthetist places a nylon sleeve (or similar) on top of the fabric sock
- Prosthetist wraps plastic film overtop of the nylon sleeve
- Prosthetist instructs the amputee to assume a neutral, slightly bent position at the elbow
- Prosthetist wets plaster cloth and wraps 2-3 layers overtop of plastic film
- Prosthetist shapes the plaster cloth around remnant limb, removing any trapped air and ensuring a good fit around any bony prominences
- Amputee waits until the plaster cloth has become firm enough for removal
- Prosthetist slides the plaster impression from the amputee's remnant limb
- Prosthetist waits for the plaster impression to dry fully
- Prosthetist marks significant features of the remnant limb on exterior of impression
- Prosthetist pours plaster into the amputee's impression
- Prosthetist inserts the metal rod handle into the plaster at the open end of the impression
- Prosthetist waits for the plaster to harden
- Once plaster dries, prosthetist cuts the plaster cloth from the exterior of the mold
- Prosthetist clamps the mold in a work station by the metal rod to allow for rotation on the rod
- Prosthetist sands the mold smooth, and adds/removes plaster to significant features Prosthetist gives the completed plaster mold to Print Center staff
Print Center staff place the mold on the 3D scanner turn table
Mold is scanned
Scan data is received by NextEngine ScanStudioHD software
Print Center staff refines the scan data within ScanStudioHD
Print Center staff exports the scan data as .XYZ file type
Print Center staff imports the .XYZ file into Solidworks modelling software and converts points into a surface model
Print Center staff saves the surface model as .STL file type
Print Center staff merges the .STL surface model file with the 'standard socket' solid model to make the 'custom fitted socket' model
Print Center staff saves the custom fitted socket model as an .STL file
Print Center staff imports the custom socket .STL file into Cura software
Print Center staff orients the model in Cura for 3D printing, sets printer settings, and saves G-Code
Print Center staff loads the G-Code file onto an SD card
Print Center staff inserts the SD card into the Ultimaker 2 3D printer and starts the print The Process to Fit an Amputee with the Prosthesis The following description covers the steps to fit a 3D printed prostheses onto an amputee.

prosthetist instructs amputee to bend their elbow to approximately 90 degrees
prosthetist rolls socket liner onto stump
prosthetist fits socket 3 onto stump
prosthetist check socket 3 for alignment
prosthetist asks amputee about socket 3 comfort
if there are any pressure points, prosthetist
   removes socket 3
   applies heat (hot air at 200 degrees C.) to appropriate area of socket 3 with heat gun until malleable
   hand forms appropriate area of socket 3
   re-checks fit of socket 3
   repeats process of heating and forming until desired fit is achieved.
if socket 3 is too far out of alignment, or if a comfortable fit cannot be achieved by heating and forming, the prosthetist communicates changes necessary to person who 3D prints the socket (print center) and a new socket 3 is printed and the fitting process begins again
Once a correctly fitting socket is ready (by determination of prosthetist), the process continues
prosthetist fits the distal end of the triceps brace 6 to the socket with socket straps 12
prosthetist attaches the triceps buckle 9 to the proximal end of the triceps brace 6 loosely with 12 mm strap
prosthetist instructs amputee to position elbow at approximately 90 degrees,
prosthetist re-fits socket 3
prosthetist adjusts socket straps 12 so that the triceps brace 6 is positioned in the middle of the posterior surface of the amputee's arm
prosthetist adjusts proximal webbing so that the triceps buckle 9 is positioned just above the belly of the biceps and below the axillary crease
prosthetist fits the axillary loop strap 11 around the unaffected arm
prosthetist ensures that the axillary padding is in place (padding the armpit)
prosthetist adjusts the straps so the harness ring 10 is centered above between the scapula and below the 7$^{th}$ cervical vertebrae
prosthetist attaches harness ring 10 to the triceps buckle 9 with the a strap coming over the amputee's shoulder
prosthetist directs amputee to lower forearm to the side
prosthetist loads socket 3 to test to see that the socket 3 is supported by the harness assembly when under load
prosthetist adjusts harness straps as necessary
prosthetist adjust the strap cable puller buckle 8 so that the cable puller buckle 8 is positioned approximately inferior to the scapula
prosthetist marks cable housing 5 length so that it terminates in the cable housing stop guide 13
prosthetist removes cable housing 5 from socket 3
prosthetist cuts cable housing 5 to length
prosthetist re-inserts cable housing 5 into socket 3 and fits to cable housing stop guide 13
prosthetist cuts cable 7 so that it terminates in cable puller buckle 8
prosthetist applies crimp to cable 7 end
prosthetist seats cable crimp in cable puller buckle 8
prosthetist glues cable puller buckle cap to cable puller buckle 8
prosthetist checks all harness straps and re-tensions as necessary Representative Computing Environment FIG. 9 depicts a generalized example of a suitable computing system 900 in which the described innovations may be implemented. The computing system 900 is not intended to suggest any limitation as to scope of use or functionality, as the innovations may be implemented in diverse general-purpose or special-purpose computing systems.

With reference to FIG. 9, the computing system 900 includes one or more processing units 910, 915 and memory 920, 925. In FIG. 9, this basic configuration 930 is included within a dashed line. The processing units 910, 915 execute computer-executable instructions. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 9 shows a central processing unit 910 as well as a graphics processing unit or co-processing unit 915. The tangible memory 920, 925 may be volatile memory (e.g., registers, cache, RAM), non-volatile memory (e.g., ROM, EEPROM, flash memory, etc.), or some combination of the two, accessible by the processing unit(s). The memory 920, 925 stores software 980 implementing one or more innovations described herein, in the form of computer-executable instructions suitable for execution by the processing unit(s).

A computing system may have additional features. For example, the computing system 900 includes storage 940, one or more input devices 950, one or more output devices 960, and one or more communication connections 970. An interconnection mechanism (not shown) such as a bus, controller, or network interconnects the components of the computing system 900. Typically, operating system software (not shown) provides an operating environment for other software executing in the computing system 900, and coordinates activities of the components of the computing system 900.

The tangible storage 940 may be removable or non-removable, and includes magnetic disks, magnetic tapes or cassettes, CD-ROMs, DVDs, or any other medium which can be used to store information and which can be accessed within the computing system 900. The storage 940 stores instructions for the software 980 implementing one or more innovations described herein.

The input device(s) 950 may be a touch input device such as a keyboard, mouse, pen, or trackball, a voice input device, a scanning device, or another device that provides input to the computing system 900. For video encoding, the input device(s) 950 may be a camera, video card, TV tuner card, or similar device that accepts video input in analog or digital form, or a CD-ROM or CD-RW that reads video samples into the computing system 900. The output device(s) 960 may be a display, printer such as a 3D printer, speaker, CD-writer, or another device that provides output from the computing system 900.

In view of the many possible embodiments to which the principles of the disclosed technology may be applied, it should be recognized that the illustrated embodiments are examples of the disclosed technology and should not be taken as a limitation on the scope of the disclosed technology. We claim all that is encompassed by the appended claims.

We claim:

1. A prosthetic wrist comprising:
   a first piece couplable to a limb socket wearable on a remnant limb of a user;
   a second piece couplable to a terminal unit;
   one of the first piece and the second piece comprising a ball and another one of the first piece and the second piece comprising a wrist socket;
   the wrist socket being removably couplable to the ball and selectively operable between:
      an unlocked state where the ball is rotatable relative to the wrist socket in a plurality of different directions to permit flexion or extension of the terminal unit relative to the limb socket; and
      a locked state where the ball is fixed relative to the wrist socket by a clamping force applied to the ball with the wrist socket to maintain a position of the terminal unit relative to the limb socket,
   the wrist socket comprising a first wrist socket portion, a second wrist socket portion, a hinge that rotatably couples the first wrist socket portion to the second wrist socket portion, and a latch that is operable with an opposite limb of the user to apply the clamping force by decreasing a separation distance between the first wrist socket portion and the second wrist socket portion and release the clamping force by increasing the separation distance between the first wrist socket portion and the second wrist socket portion.

2. The wrist of claim 1, wherein:
   exterior surfaces of the ball define a convex shape; and
   interior surfaces of the wrist socket define a concave shape operable to interface with the convex shape.

3. The wrist of claim 2, wherein the clamping force establishes a friction fit between the convex shape and the concave shape.

4. The wrist of claim 3, wherein one or both of the convex shape and the concave shape are configured to affect a frictional coefficient between the interior surfaces and the exterior surfaces.

5. The wrist of claim 3, wherein one or both of:
   the convex shape comprises a pattern of thin grooves; and
   the concave shape comprises an elastomeric lining.

6. The wrist of claim 1, wherein the latch is pivotally attached to the wrist socket so that the clamping force is adjustable by pivoting the latch toward the wrist with the opposite limb of the user and releasable by pivoting the latch away from the wrist with the opposite limb of the user.

7. The wrist of claim 1, wherein:
   the first wrist socket portion defines a first concave surface operable to interface with a first portion of the ball; and
   the second wrist socket portion defines a second concave surface operable to interface with a second portion of the ball.

8. The wrist of claim 7, wherein the latch is operable to cause:
   the first concave surface of the first wrist socket portion to apply a first part of the clamping force to the first portion of the ball; and
   the second concave surface of the second wrist socket portion to apply a second part of the clamping force to the second portion of the ball.

9. The wrist of claim 8, wherein the latch is selectively operable to adjust the clamping force by changing a separation distance between the first concave surface of the first wrist socket portion and the second concave surface of the second wrist socket portion.

10. The wrist of claim 1, comprising a first hole extending through the wrist socket and a second hole extending through the ball, the first and second holes being capable of directing a cable into the terminal unit through the wrist socket and the ball.

11. The wrist of claim 10, wherein exterior surfaces of the ball define a semi-spherical convex shape and the second hole extends through an end face of the semi-spherical convex shape.

12. The wrist of claim 10, comprising a plurality of connector holes extending through the ball at locations adjacent the second hole.

13. The wrist of claim 1, wherein the first piece and the second piece are 3D printed structures.

14. The wrist of claim 11, wherein the end face of the ball comprises a concave shape extending into the semi-spherical convex shape around the second hole.

15. A system comprising:
   the prosthetic wrist of claim 10; and
   the limb socket, in which the limb socket comprises a channel that extends through an interior of the limb socket and is capable of directing the cable through the interior of the limb socket and into the first hole of the wrist socket or the second hole of the ball.

16. The system of claim 15, comprising:
   the cable; and
   a cable housing that passes along an exterior surface of the limb socket, enters the interior of the limb socket through the channel, and is capable of directing the cable into the interior of the limb socket.

17. The system of claim 16, wherein the limb socket comprises a cable rotation guide capable of directing the cable housing into the interior of the limb socket and allowing a portion of the cable housing to pivot relative to the limb socket.

18. A system comprising:
   the prosthetic wrist of claim 1; and
   one or more of:
      the limb socket;
      the terminal unit;
      a tricep brace; and
      a harness.

19. The system of claim 17, wherein the prosthetic wrist, the limb socket, and the terminal unit, the tricep brace, and the harness comprise 3D printed structures.

\* \* \* \* \*